US011376235B2

(12) United States Patent
Watanabe et al.

(10) Patent No.: US 11,376,235 B2
(45) Date of Patent: Jul. 5, 2022

(54) INHIBITOR OF INFLAMMASOME ACTIVATION

(71) Applicant: KRACIE HOLDINGS, LTD., Tokyo (JP)

(72) Inventors: Shimpei Watanabe, Tokyo (JP); Ayako Arai, Tokyo (JP); Yuichi Takajo, Tokyo (JP); Satoshi Inamasu, Tokyo (JP); Satoshi Yomoda, Tokyo (JP); Akiko Ohno, Tokyo (JP); Yuko Kitahara, Tokyo (JP); Taisaku Kanatani, Tokyo (JP)

(73) Assignee: KRACIE HOLDINGS, LTD., Tokyo (JP)

( * ) Notice: Subject to any disclaimer, the term of this patent is extended or adjusted under 35 U.S.C. 154(b) by 274 days.

(21) Appl. No.: 16/076,092

(22) PCT Filed: Feb. 8, 2017

(86) PCT No.: PCT/JP2017/004648
§ 371 (c)(1),
(2) Date: Aug. 7, 2018

(87) PCT Pub. No.: WO2017/138586
PCT Pub. Date: Aug. 17, 2017

(65) Prior Publication Data
US 2019/0099400 A1    Apr. 4, 2019

(30) Foreign Application Priority Data

Feb. 8, 2016  (JP) .............................. JP2016-021844

(51) Int. Cl.
| | | |
|---|---|---|
| *A61K 36/00* | (2006.01) |
| *A61K 31/365* | (2006.01) |
| *A61K 31/7048* | (2006.01) |
| *A61K 36/28* | (2006.01) |
| *A61K 36/634* | (2006.01) |
| *A23L 33/105* | (2016.01) |
| *A61Q 19/00* | (2006.01) |
| *A61K 8/97* | (2017.01) |
| *A61K 8/49* | (2006.01) |
| *A61P 3/10* | (2006.01) |
| *A61P 17/06* | (2006.01) |
| *A61P 25/16* | (2006.01) |
| *A61P 9/00* | (2006.01) |
| *A61P 1/16* | (2006.01) |
| *A61P 27/02* | (2006.01) |
| *A61P 13/12* | (2006.01) |
| *A61P 9/10* | (2006.01) |
| *A61P 29/00* | (2006.01) |
| *A61P 3/04* | (2006.01) |
| *A61P 17/10* | (2006.01) |
| *A61P 25/28* | (2006.01) |
| *A61P 17/00* | (2006.01) |
| *A61P 17/14* | (2006.01) |
| *A61K 8/9789* | (2017.01) |
| *A61K 8/60* | (2006.01) |

(52) U.S. Cl.
CPC .......... *A61K 31/365* (2013.01); *A23L 33/105* (2016.08); *A61K 8/49* (2013.01); *A61K 8/4973* (2013.01); *A61K 8/602* (2013.01); *A61K 8/97* (2013.01); *A61K 8/9789* (2017.08); *A61K 31/7048* (2013.01); *A61K 36/28* (2013.01); *A61K 36/634* (2013.01); *A61P 1/16* (2018.01); *A61P 3/04* (2018.01); *A61P 3/10* (2018.01); *A61P 9/00* (2018.01); *A61P 9/10* (2018.01); *A61P 13/12* (2018.01); *A61P 17/00* (2018.01); *A61P 17/06* (2018.01); *A61P 17/10* (2018.01); *A61P 17/14* (2018.01); *A61P 25/16* (2018.01); *A61P 25/28* (2018.01); *A61P 27/02* (2018.01); *A61P 29/00* (2018.01); *A61Q 19/00* (2013.01); *A23V 2002/00* (2013.01); *A23V 2200/30* (2013.01); *A23V 2250/21* (2013.01)

(58) Field of Classification Search
None
See application file for complete search history.

(56) References Cited

U.S. PATENT DOCUMENTS

2010/0104524 A1    4/2010  Lee et al.

FOREIGN PATENT DOCUMENTS

| CN | 102 397 548 | 4/2012 |
| CN | 102 805 743 | 12/2012 |

(Continued)

OTHER PUBLICATIONS

Kim et al. (Screening and Biotransformation of Interleukin-1 Converting Enzyme Production Inhibitors from Arctii fructus, J. Microbiol. Biotechnol., 2005, 15(2), pp. 269-273, within the IDS) (Year: 2005).*
Park et al. ("Hepatoprotective Effect of Herb Formula KIOM2012H against Nonalcoholic Fatty Liver Disease", Nutrients 2015, 7, 244-2455, doi: 10.3390/nu7042440, published Apr. 2, 2015). (Year: 2015).*
Yuk-Shing Chan, et al, "A Review of the Pharmacological Effects of Arctium appa," (2011) 19 Inflammopharmacology 245.

(Continued)

*Primary Examiner* — Michael Barker
*Assistant Examiner* — Randall O Winston
(74) *Attorney, Agent, or Firm* — Greenblum & Bernstein, P.L.C.

(57) ABSTRACT

To provide a novel inflammasome inhibitor capable of inhibiting activation of inflammasome, the present inventors newly found that arctigenin reduces the amount of 1L-1β released and the amount of activated caspase-1 upon stimulation with ATP, palmitic acid, MSU and Poly(dA:dT) and thus has an effect of inhibiting inflammasome activation. The present invention provides an inhibitor of inflammasome activation that comprises arctigenin as an active ingredient.

2 Claims, 7 Drawing Sheets

(56) References Cited

FOREIGN PATENT DOCUMENTS

| | | |
|---|---|---|
| CN | 103933056 A | 7/2014 |
| CN | 104 138 387 | 11/2014 |
| CN | 104138387 A | 11/2014 |
| JP | 2008 297209 | 12/2008 |
| JP | 2010-520233 | 6/2010 |
| JP | 2013-545767 A | 12/2013 |
| JP | 2014-094917 | 5/2014 |
| WO | 2008/105605 | 9/2008 |
| WO | 2012/074183 A1 | 6/2012 |
| WO | 2013 / 007763 | 1/2013 |
| WO | WO2013007763 A1 * | 1/2013 |
| WO | 2015/016178 | 2/2015 |

OTHER PUBLICATIONS

Ji Yun Lee, et al., "Arctigenin, a Phenylpropanoid Dibenzylbutyrolactone Lignan, Inhibits Type I-IV Allergic Inflammation and Pro-inflammatory Enzymes," (2010) 33 Archives of Pharmacal Resserch, 947.
Office Action issued by Japanese Patent Office in Application JP2017525435 dated Oct. 1, 2018.
Tao Fan et al, Biological & Pharmaceutical Bulletin (of Japan), vol. 35, No. 11, Jan. 1, 2012, pp. 2004-2009.
Dongwei Li el at , Planta Medica, vol. 80, No. 01, Jan. 10, 2014, pp. 48-55.
Zeng Xiao-Yan et al , Fitoterapia, vol. 105, Sep. 2015, pp. 119-126.
Ji Yun Lee et al, Archives of Pharmaceutical Research, vol. 33, No. 6, Jun. 1, 2010, pp. 947-957.
Seunghee Bae et al, Biological Research, Biomed Central LTD, London, UK, vol. 47, No. 1, Sep. 30, 2014, p. 50.
Anonymous, ScienceDirect, Jan. 17, 2020, p. 1-8, URL:http://www.sciencedirect.com/topics/medicine-and-dentistry/autoinflammatory-disease.
Z. Zhu et al, The Journal of Neuroscience, vol. 33, No. 32, Aug. 7, 2013, pp. 13138-13149.
European Search Report, European Patent Office, Application No. 17750307.5, dated Aug. 6, 2019.
European Search Report, European Patent Office, Application No. 17750307.5, dated Jan. 24, 2020.
International Search Report issued in International Patent Appl. No. PCT/JP2017/004648, dated Mar. 7, 2017.
Naoki Hata, "Arctiin Arctigenin no Takinosei to Kogan'yu Shokubutsu no Riyo", Agriculture and horticulture, B6 (1), 2011, pp. 10-20, 13-15 & 15-17, including partial translation thereof.
Hyun-A Kim et al., "Screening and Biotransformation of Interleukin-1B Converting Enzyme Production Inhibitors from Arctii fructus", J. Microbiol. & Biotechnol., 15 (2), 2005, pp. 269-273.
International Preliminary Report on Patentability issued in International Patent Appl. No. PCT/JP2017/004648, dated Aug. 14, 2018.
Szabo et al., "Inflammasome activation and function in liver disease", Nature Reviews / Gastroenterology & Hepatology, vol. 12, No. 7, Jul. 2015, pp. 387-400.
Wielinga et al., "P239 Metabolic Syndrome and Non-Alcoholic Steatohepatitis (NASH) are Attenuated by Intervention With Caspase-1 Inhibitor in High Fat Diet Fed LDLR-/- Leiden Mice", Journal of Hepatology, vol. 60, Apr. 2014, p. S145.
Ouyang et al., "Su 10578 Low Dose Digoxin Protects From NASH and Alcoholic Hepatitis in Mice by Inhibiting Inflammasome Activity and Mitochondrial ROS Production", Gastroenterology, vol. 148, No. 4, Apr. 1, 2015, pp. S-1052.
Office Action for corresponding EP Application No. 17750307.5, dated Sep. 1, 2020.

* cited by examiner

INHIBITOR OF INFLAMMASOME ACTIVATION

DETAILED DESCRIPTION OF INVENTION

Technical Field

The present invention relates to an inhibitor of inflammasome activation, a composition for inhibiting inflammasome activation and a food composition for inhibiting inflammasome activation.

Background Art

Inflammasomes are complexes of a plurality of protein and are considered to play an important role in inducing or promoting inflammatory responses. An inflammasome is composed of a pattern recognition receptor such as NOD-like receptors (NLRs) including NLRC4, NLRP1, NLRP3 and the like or AIM2 (absent in melanoma 2), an adaptor protein ASC (apoptosis-associated speck-like protein containing caspase recruitment domain) and a caspase-1 precursor. When NLRC4, NLRP1, NLRP3 and AIM2 recognize an exogenous or endogenous danger signal, an inflammasome is formed, and, as a result, caspase-1 is activated. The activated caspase-1 (hereinafter referred to as "activated caspase-1" or "caspase-1" simply) activates inflammatory cytokines such as IL-1β and IL-18.

Inflammasomes are activated by exogenous factors such as pathogen components, UV irradiation and asbestos and by endogenous factors such as ATP, cholesterol crystals, amyloid β, saturated fatty acids and urate crystals (MSU). Inflammasomes play a central role in the onset and the progress of infectious diseases, autoinflammatory diseases, allergic diseases, age-related macular degeneration, cardiovascular diseases, ischemic injury, gout, dementia, obesity-related inflammatory diseases and the like. Therefore, new therapeutic methods, for these diseases, which target inflammasomes have been developed.

It is also known that chronic inflammation is initiated by inflammasome activation with age. This is chronic inflammation that is irrelevant to infection immunity and that lasts long in the body and is a pathological condition underlying various diseases such as obesity, diabetes, cancers, neurodegenerative diseases and autoimmune diseases. This is supported also by the fact that the concentrations of inflammatory cytokines such as CRP, IL-6 and TNF-α are high in elderly people even when the elderly people do not show any clear sign of infectious diseases and the like. Therefore, the regulation of chronic inflammation is important to achieve a long healthy life.

As a drug that inhibits inflammasome activation, for example, PTL 1 discloses an inhibitor of inflammasome activation comprising isoliquiritigenin, liquiritigenin or glycyrrhizin as an active ingredient.

CITATION LIST

Patent Literature

[PTL 1] Publication of Japanese Patent Application "JP-A-2014-094917"

SUMMARY OF INVENTION

Technical Problem

An object of the invention is to provide a novel inhibitor of inflammasome activation which can inhibit inflammasome activation in order to establish a new therapeutic method for various inflammasome-related diseases.

Solution to Problem

As a result of intensive investigation to solve the above problem, the present inventors have found that arctigenin has the effect of inhibiting inflammasome activation. The inventors differentiated monocytic cells into macrophage-like cells by PMA (phorbol 12-myristate acetate) treatment, then induced the expression of IL-1β precursor by LPS treatment and, after treatment with arctigenin, activated inflammasomes by treating with NLRP3 inflammasome inducers (ATP, palmitic acid and MSU) and an AIM2 inflammasome inducer (Poly(dA:dT)).

As a result, the inventors have found that arctigenin reduces the amount of 1L-1β released and the amount of activated caspase-1 upon stimulation with ATP, palmitic acid, MSU and Poly(dA:dT). Thus, it has been strongly suggested that arctigenin has the effects of inhibiting the activation of NLRP3 inflammasome by ATP, palmitic acid and MSU and the activation of AIM2 inflammasome by Poly(dA:dT). It is also known that arctiin, which is a precursor of arctigenin, is metabolized in the living body and converted into arctigenin, and it is thus expected that arctiin has the same effects as those of arctigenin.

The invention provides an inhibitor of inflammasome activation comprising arctigenin and/or arctiin as an active ingredient.

The invention also provides a composition for inhibiting inflammasome activation comprising arctigenin and/or arctiin as an active ingredient.

The invention also provides the above composition for inhibiting inflammasome activation in which arctigenin and/or arctiin is comprised in the form of burdock, burdock fruit, burdock sprout, *forsythia* or an extract thereof.

The invention also provides a pharmaceutical product comprising the above composition for inhibiting inflammasome activation.

The invention also provides a cosmetic product comprising the above composition for inhibiting inflammasome activation.

The invention also provides a food composition for inhibiting inflammasome activation comprising arctigenin and/or arctiin as an active ingredient.

The invention provides a food composition for inhibiting inflammasome activation in which the above arctigenin and/or the above arctiin is comprised in the form of burdock, burdock fruit, burdock sprout, *forsythia* leave or an extract thereof.

The invention also provides a method for inhibiting inflammasome activation including a step of administering arctigenin and/or arctiin to a subject. In the method of the invention, arctigenin and/or arctiin may be administered in the form of burdock, burdock fruit, burdock sprout, *forsythia* or an extract thereof.

The invention also provides arctigenin and/or arctiin for use in the inhibition of inflammasome activation.

The invention also provides use of arctigenin and/or arctiin for the inhibition of inflammasome activation. In the use of the invention, arctigenin and/or arctiin may be used in a form comprised in burdock, burdock fruit, burdock sprout, *forsythia* or an extract thereof.

The invention also provides use of arctigenin and/or arctiin for the manufacture of an inhibitor of inflammasome activation. In the use of the invention, arctigenin and/or arctiin may be used in a form comprised in burdock, burdock fruit, burdock sprout, *forsythia* or an extract thereof.

The invention also provides an inhibitor of caspase-1 production comprising arctigenin and/or arctiin as an active ingredient. The invention also provides a composition for inhibiting caspase-1 production comprising arctigenin and/or arctiin as an active ingredient. The invention also provides a food composition for inhibiting caspase-1 production comprising arctigenin and/or arctiin as an active ingredient. Arctigenin and/or arctiin may be comprised in the form of burdock, burdock fruit, burdock sprout, *forsythia* or an extract thereof.

The invention also provides a method for inhibiting caspase-1 production including a step of administering arctigenin and/or arctiin to a subject. In the method of the invention, arctigenin and/or arctiin may be administered in the form of burdock, burdock fruit, burdock sprout, *forsythia* or an extract thereof.

The invention also provides arctigenin and/or arctiin for use in the inhibition of caspase-1 production.

The invention also provides use of arctigenin and/or arctiin for the inhibition of caspase-1 production. In the use of the invention, arctigenin and/or arctiin may be used in a form comprised in burdock, burdock fruit, burdock sprout, *forsythia* or an extract thereof.

The invention also provides use of arctigenin and/or arctiin for the manufacture of an inhibitor of caspase-1 production. In the use of the invention, arctigenin and/or arctiin may be used in a form comprised in burdock, burdock fruit, burdock sprout, *forsythia* or an extract thereof.

Advantageous Effects of Invention

According to the invention, inflammasome activation can be inhibited effectively, and thus a new therapeutic method for treating, improving and preventing various inflammasome-related diseases can be established.

DESCRIPTION OF EMBODIMENTS

The invention provides an inhibitor of inflammasome activation which inhibits inflammasome activation.

In the invention, the inflammasome is a protein complex composed of a pattern recognition receptor such as NLRC4, NLRP1, NLRP3 and AIM2, ASC (apoptosis-associated speck-like protein containing caspase recruitment domain) and a caspase-1 precursor. The inflammasome which is the target of the inhibitor of inflammasome activation of the invention is not particularly limited and can be, for example, NLRP3 inflammasome, AIM2 inflammasome and the like.

The "inflammasome activation" herein means that an inflammasome is formed by association of a pattern recognition receptor such as NLRP3 and AIM2 with ASC and a caspase-1 precursor due to a stimulating factor such as ATP, saturated fatty acids, MSU and pathogen components and that caspase-1 is activated. The inhibitor of inflammasome activation of the invention inhibits this inflammasome activation and thus inhibits the production of activated caspase-1. As a result, the inhibitor of inflammasome activation of the invention can further inhibit the release of an inflammatory cytokine such as IL-1α, IL-1β, IL-6, IL-18, IL-33, TNF-α and HMGB1.

"To inhibit inflammasome activation" herein means to completely or partially inhibit the inflammasome activation by a stimulating factor. In other words, "to inhibit inflammasome activation" means to reduce the amount of produced activated caspase-1 or the amount of released inflammatory cytokine as compared to the case without the treatment with the inhibitor of inflammasome activation of the invention.

"To inhibit caspase-1 production" herein means to reduce the amount of caspase-1 (activated caspase-1) (production amount) or to inhibit an increase in the amount of caspase-1 (activated caspase-1) (production amount).

The inhibitor of inflammasome activation of the invention comprises arctigenin and/or arctiin as an active ingredient. Arctigenin and arctiin are one of diphenylpropanoids (lignans) contained in plants such as burdock. Arctiin is a precursor of arctigenin and is known to be metabolized and converted into arctigenin in the living body. As arctigenin and/or arctiin, chemically synthesized arctigenin and/or arctiin may be used, and arctigenin and/or arctiin isolated from a plant may also be used. Moreover, as arctigenin and/or arctiin, a plant itself containing arctigenin and/or arctiin or an extract which is extracted from a plant may be used. Examples of plants containing arctigenin and/or arctiin include *Arctium lappa* (burdock) (sprouts, leaves, rhizomes and burdock fruit), *Forsythia×intermedia* (flowers, leaves, fruits and rhizomes), *Forsythia viridissima* var. *koreana* (flowers, leaves, fruits and rhizomes), *Forsythia suspensa* (*forsythia*) (flowers, leaves, fruits and rhizomes), *Forsythia viridissima* (flowers, leaves, fruits and rhizomes), *Carthamus tinctorius, Centaurea cyanus, Cirsium vulgare, Centaurea benedicta* (*Cnicus benedictus*), *Cynara cardunculus, Onopordum acanthium*, thistle (Aniurokoazami), *Sesamum indicum, Ipomoea cairica, Polygala chinensis, Trachelospermum asiaticum* var. *glabrum, Trachelospermum asiaticum, Trachelospermum gracilipes* var. *liukiuense, Trachelospermum gracilipes, Trachelospermum jasminoides, Trachelospermum jasminoides* var. *pubescens, Wikstroemia indica, Persicaria orientalis, Cerasus jamasakura, Arabidopsis thaliana*, amaranth, *Juglans* (walnut), *Avena sativa* (oat), *Triticum spelta*, soft wheat, *Cupressus lusitanica* and *Torreya nucifera*. Of these examples, burdock (in particular, burdock fruit and burdock sprout) and *forsythia* (in particular, leaves) are preferable because the arctigenin and/or arctiin contents are high. When a plant itself is used, a raw or dry cut plant or dry powder of the plant can be used.

When an extract extracted from a plant is used as arctigenin and/or arctiin, the extract may be prepared from the plant, for example, by the following method. For example, the extract used in the invention may be extracted from a plant containing arctigenin and/or arctiin by two stages, namely an enzymatic conversion step and an extraction step using an organic solvent.

The enzymatic conversion step is a step of enzymatically converting arctiin contained in a plant into arctigenin by β-glucosidase, which is an endogenous enzyme of the plant. Specifically, by drying and cutting the plant and then keeping the plant at an appropriate temperature, endogenous β-glucosidase is caused to act, and the reaction from arctiin to arctigenin is advanced. For example, by adding a solution such as water to the cut plant and stirring them at a temperature of around 30° C. (20 to 50° C.) or by another procedure, the plant can be kept at a certain temperature.

The extraction step using an organic solvent is a step of extracting arctigenin and arctiin from a plant using an appropriate organic solvent. That is, this is a step of extracting an extract from the plant by adding an appropriate solvent in the condition that the arctigenin content of the plant has become high through the above enzymatic conversion step. For example, an extract is extracted by adding an appropriate solvent to the plant and heating and stirring for an appropriate period of time. The extract can also be extracted using any extraction method known to one skilled in the art, such as heat-reflux, drip extraction, immersion extraction or a pressurized extraction method, in addition to heating and stirring.

Because arctigenin is insoluble in water, the yield of arctigenin can be improved by adding an organic solvent. As the organic solvent, any organic solvent can be used. For example, alcohols such as methanol, ethanol and propanol and acetone can be used. In view of the safety, 30% ethanol is preferably used as the organic solvent in the production method of the extract used for the inhibitor of inflammasome activation of the invention. When the solvent is evaporated from the extract, a paste-like concentrate is obtained, and a dried product can be obtained by further drying the concentrate.

The inhibitor of inflammasome activation of the invention can be a pharmaceutical preparation in any form. For example, the inhibitor of inflammasome activation as an orally-administered pharmaceutical preparation can be: a tablet such as sugar-coated tablets, buccal tablets, coating tablets and chewable tablets; a troche; a pill; powder; a capsule including hard capsules and soft capsules; granules; a liquid such as suspensions, emulsions, syrups and elixirs; and the like.

In addition, the inhibitor of inflammasome activation of the invention can be a pharmaceutical preparation for parenteral administration such as intravenous injection, subcutaneous injection, intraperitoneal injection, intramuscular injection, transdermal administration, nasal administration, transpulmonary administration, enteral administration, buccal administration and transmucosal administration. For example, the inhibitor of inflammasome activation of the invention can be an injection, a transdermal absorbing tape, an aerosol, a suppository and the like.

The inhibitor of inflammasome activation of the invention can also be provided as an external preparation. The external preparation of the invention can be a pharmaceutical product, a cosmetic product and the like. The external preparation of the invention can be an external preparation applied to the skin, scalp, hair, mucous membranes, nails and the like. Examples of the external preparation include: preparations to be applied such as creams, ointments, liquids, gels, lotions, emulsions, aerosols, sticks, sheet masks, solids, foams, oils and hard gel sticks; preparations to be attached such as cataplasms, plasters, tapes and patches; spray preparations; and the like.

The inhibitor of inflammasome activation of the invention can also be in a form suitable for foods and may be, for example, a solid, a liquid, granules, grains, powder, capsules, a cream, a paste and the like.

Moreover, the invention provides a composition for inhibiting inflammasome activation comprising arctigenin and/or arctiin as an active ingredient. The composition for inhibiting inflammasome activation of the invention can be composed in a manner similar to that of the inhibitor of inflammasome activation described above. The composition for inhibiting inflammasome activation of the invention can be a composition used for pharmaceutical products, cosmetic products, foods and the like. The composition for inhibiting inflammasome activation of the invention can further contain any component which is generally used for pharmaceutical products, cosmetic products and foods. For example, the composition for inhibiting inflammasome activation of the invention may further contain a base, a carrier, an excipient, a binder, a disintegrating agent, a lubricant and a coloring agent and the like which are pharmaceutically acceptable.

Examples of the carrier and the excipient used for the composition for inhibiting inflammasome activation include lactose, glucose, white soft sugar, mannitol, dextrin, potato starch, corn starch, calcium carbonate, calcium phosphate, calcium sulfate, crystalline cellulose and the like.

Examples of the binder include starch, gelatin, syrup, tragacanth gum, polyvinyl alcohol, polyvinyl ether, polyvinylpyrrolidone, hydroxypropylcellulose, methylcellulose, ethylcellulose, carboxymethylcellulose and the like.

Examples of the disintegrating agent include starch, agar, gelatin powder, crystalline cellulose, calcium carbonate, sodium hydrogen carbonate, sodium alginate, sodium carboxymethylcellulose, calcium carboxymethylcellulose and the like.

Examples of the lubricant include magnesium stearate, hydrogenated vegetable oil, talc, macrogol and the like. As the coloring agent, any coloring agent which has been accepted to be added to pharmaceutical products, cosmetic products and foods can be used.

In addition, the composition for inhibiting inflammasome activation, if required, may be coated with one or more layers of white soft sugar, gelatin, refined shellac, gelatin, glycerin, sorbitol, ethylcellulose, hydroxypropylcellulose, hydroxypropylmethylcellulose, polyvinylpyrrolidone, phthalic acid cellulose acetate, hydroxypropylmethylcellulose phthalate, methyl methacrylate, a methacrylic acid polymer and the like.

Moreover, if required, a pH-controller, a buffering agent, a stabilizer, a preservative, an antiseptic, a diluent, a coating agent, a sweetener, an aroma, a solubilizing agent and the like may be added to the composition for inhibiting inflammasome activation.

The invention also provides a pharmaceutical product comprising the composition for inhibiting inflammasome activation of the invention. The pharmaceutical product of the invention can be a pharmaceutical product for inhibiting inflammasome activation, namely an inhibitor of inflammasome activation. Moreover, the pharmaceutical product of the invention can be a pharmaceutical product for treating, improving or preventing a disease such as infectious diseases, autoinflammatory diseases, allergic diseases, age-related macular degeneration, cardiovascular diseases, ischemic injury, gout, obesity-related inflammatory diseases (diabetes, steatohepatitis, arteriosclerosis and the like) and inflammatory skin diseases (psoriasis, alopecia, acne vulgaris, atopic dermatitis and the like) and a condition thereof. Moreover, evidences which have been found suggest that symptoms of various diseases that advance with age, such as cancers, dyslipidemia, gout, CKD (chronic kidney disease), NASH (non-alcoholic steatohepatitis), Alzheimer-type dementia, Parkinson's disease, cerebral apoplexy and chronic rheumatoid arthritis, and even ageing itself advance with chronic inflammatory changes by inflammasome activation, and the pharmaceutical product of the invention can be a pharmaceutical product for treating, improving or preventing any of these diseases and conditions.

The invention also provides a cosmetic product comprising the composition for inhibiting inflammasome activation of the invention. The cosmetic product of the invention can be a cosmetic product for improving or preventing a disease such as infectious diseases, autoinflammatory diseases, allergic diseases, age-related macular degeneration, cardiovascular diseases, ischemic injury, gout, dementia, obesity-related inflammatory diseases (diabetes, steatohepatitis, arteriosclerosis and the like) and inflammatory skin diseases (psoriasis, alopecia, acne vulgaris, atopic dermatitis and the like) and a condition thereof and especially can be a cosmetic product for improving or preventing an inflammatory skin disease (psoriasis, alopecia, acne vulgaris, atopic dermatitis and the like) and a condition thereof.

The cosmetic product of the invention can be applied, for example, to the skin (face, fingers, whole body and the like), scalp, hair, mucous membranes, nails, eyelashes, eyebrows and/or the like. Examples of the cosmetic product of the invention can be: skin-washing cosmetics such as facial washing cream, facial washing foam, facial cleansing products, bar soap, body soap and hand soap; skin-care cosmetics such as face lotion, milky lotion, cream, gel, sheet masks, beauty oil and beauty essence; makeup cosmetics such as foundation, lipstick, face color, eye liner and cosmetic primer; antiperspirants; sunscreens; hair-washing products such as shampoo and conditioner; hair or scalp cosmetics such as hair spray, hair mousse, hair foam, hair oil, hair mist, hair water, hair lotion, hair blow products, hair milk, hair cream, hair treatment, hair mask, hair gel, hair balm, hair tonic and hair liquid; and the like.

The invention also provides a food composition for inhibiting inflammasome activation comprising arctigenin and/or arctiin as an active ingredient. The food composition for inhibiting inflammasome activation of the invention can be composed in a manner similar to those of the inhibitor of inflammasome activation and the composition for inhibiting inflammasome activation described above. The food composition of the invention can be a food composition for improving or preventing a disease such as infectious diseases, autoinflammatory diseases, allergic diseases, age-related macular degeneration, cardiovascular diseases, ischemic injury, gout, dementia, obesity-related inflammatory diseases (diabetes, steatohepatitis, arteriosclerosis and the like) and inflammatory skin diseases (psoriasis, alopecia, acne vulgaris, atopic dermatitis and the like) and a condition thereof.

The "food composition" herein includes not only general foods and drinks but also foods for the ill, health foods, functional foods, foods for specified health use, dietary supplements, supplements and the like. Examples of the general foods and drinks include various drinks, various foods, processed foods, liquid foods (soups and the like), seasonings, nutrition-supplement drinks, snacks and the like. The "processed foods" herein mean foods obtained by processing and/or cooking natural foodstuffs (animals, plants and the like) and include, for example, processed meat, processed vegetables, processed fruits, frozen foods, retort-pouched foods, canned foods, bottled foods, instant foods and the like. The food composition of the invention may be a food with an indication saying that inflammasome activation is inhibited. The food composition of the invention may also be provided in a form contained in a bag, a container and the like. The bag and the container used in the invention can be any bag and any container which are generally used for foods.

The invention also provides a method for inhibiting inflammasome activation including a step of administering arctigenin and/or arctiin to a subject. The invention also provides a method for inhibiting inflammasome activation including a step of causing a subject to take arctigenin and/or arctiin. In the method of the invention, arctigenin and/or arctiin may be administered in the form of burdock, burdock fruit, burdock sprout, *forsythia* or an extract thereof.

The subjects to which the methods of the invention are applied include mammals such as humans, mice, rats, rabbits, cats, dogs, cattle, horses, monkeys and the like. The subject of the administration or the subject of the intake in the methods of the invention can be a subject in need of the inhibition of inflammasome activation. The subject in need of the inhibition of inflammasome activation can be a subject having various diseases, such as infectious diseases, autoinflammatory diseases, allergic diseases, age-related macular degeneration, cardiovascular diseases, ischemic injury, gout, obesity-related inflammatory diseases (diabetes, steatohepatitis, arteriosclerosis and the like), inflammatory skin diseases (psoriasis, alopecia, acne vulgaris, atopic dermatitis and the like) and diseases that advance with age including cancers, dyslipidemia, CKD (chronic kidney disease), NASH (non-alcoholic steatohepatitis), Alzheimer-type dementia, Parkinson's disease, cerebral apoplexy and chronic rheumatoid arthritis, and the symptoms thereof. The methods of the invention can treat, improve or prevent the diseases described above and the symptoms thereof.

The invention also provides arctigenin and/or arctiin for use in the inhibition of inflammasome activation. The invention also provides arctigenin and/or arctiin for use in the treatment, the improvement or the prevention of any of various diseases and symptoms caused by inflammasome activation, such as infectious diseases, autoinflammatory diseases, allergic diseases, age-related macular degeneration, cardiovascular diseases, ischemic injury, gout, obesity-related inflammatory diseases (diabetes, steatohepatitis, arteriosclerosis and the like), inflammatory skin diseases (psoriasis, alopecia, acne vulgaris, atopic dermatitis and the like) and diseases that advance with age including cancers, dyslipidemia, CKD (chronic kidney disease), NASH (non-alcoholic steatohepatitis), Alzheimer-type dementia, Parkinson's disease, cerebral apoplexy and chronic rheumatoid arthritis, and symptoms thereof.

The invention also provides use of arctigenin and/or arctiin for the inhibition of inflammasome activation. In the use of the invention, arctigenin and/or arctiin may be used in a form comprised in burdock, burdock fruit, burdock sprout, *forsythia* or an extract thereof.

The invention also provides use of arctigenin and/or arctiin for the manufacture of an inhibitor of inflammasome activation, a composition for inhibiting inflammasome activation or a food composition for inhibiting inflammasome activation. In the use of the invention, arctigenin and/or arctiin may be used in a form comprised in burdock, burdock fruit, burdock sprout, *forsythia* or an extract thereof.

The invention also provides an inhibitor of caspase-1 production, a composition for inhibiting caspase-1 production and a food composition for inhibiting caspase-1 production each comprising arctigenin and/or arctiin as an active ingredient. The inhibitor of caspase-1 production, the composition for inhibiting caspase-1 production and the food composition for inhibiting caspase-1 production of the invention can be composed in manners similar to those of the inhibitor of inflammasome activation, the composition for inhibiting inflammasome activation and the food composition for inhibiting inflammasome activation described above.

The inhibitor of caspase-1 production, the composition for inhibiting caspase-1 production and the food composition for inhibiting caspase-1 production of the invention inhibit the production of caspase-1 and can thus inhibit the release of an inflammatory cytokine. Thus, the inhibitor of caspase-1 production, the composition for inhibiting caspase-1 production and the food composition for inhibiting caspase-1 production of the invention can be used for treating, improving or preventing a disease such as infectious diseases, autoinflammatory diseases, allergic diseases, age-related macular degeneration, cardiovascular diseases, ischemic injury, gout, obesity-related inflammatory diseases (diabetes, steatohepatitis, arteriosclerosis and the like) and inflammatory skin diseases (psoriasis, alopecia, acne vulgaris, atopic dermatitis and the like) and a condition thereof.

EXAMPLES

Although Examples are shown below and the embodiments of the invention are explained in further detail, the invention is not limited to the Examples below.
(Measurement of Enzymatic Activity)

The β-glucosidase activities of burdock fruit were measured by the following method. Burdock fruit samples of different origins and different lots were pulverized with a Wiley mill, and the pulverized burdock fruit samples each in an amount of 0.1 g were diluted with 10 mL of water, sample solutions were thus obtained.

As the substrate solution, a 20 mmol/L aqueous solution of p-nitrophenyl-β-D-glucopyranoside was prepared by adding water to 0.15 g of p-nitrophenyl-β-D-glucopyranoside and adjusting the volume to 25 mL. To 1 mL of a 0.1 mol/L acetic acid buffer, 0.5 mL of the 20 mmol/L p-nitrophenyl-β-D-glucopyranoside aqueous solution was added, and a reaction mixture was thus prepared and then preheated at 37° C. for approximately five minutes.

After adding 0.5 mL of a sample solution to the reaction mixture and advancing the reaction at 37° C. for 15 minutes, the reaction was stopped by adding 2 mL aqueous solution of a 0.2 mol/L sodium carbonate, which is a solution to stop the reaction. The absorbance of this liquid at 400 nm was measured, and the enzymatic activity was determined using the following equation from the variation from the value of the blank solution which was not subjected to the enzymatic reaction. Enzymatic activity (U/g)=(absorbance of sample solution−absorbance of blank solution)×4 mL×1/18.1 (millimolar molecular extinction coefficient of p-nitrophenol under the above measurement conditions: $cm^2/\mu mol$)×1/optical path length (cm)×1/reaction period (minute)×1/0.5 mL×1/concentration of sample solution (g/mL).

Example 1 Production of Burdock Fruit Extract 1

As an Example of the composition for inhibiting inflammasome activation of the invention, an extract was extracted from burdock fruit. After cutting burdock fruit (enzymatic activity of 8.23 U/g), the pieces which completely passed through a sieve of 9.5 mm were further passed through a sieve of 0.85 mm, and it was confirmed that 75% thereof remained. To 560 L of water which was kept at 29 to 33° C., 80 kg of the cut burdock fruit pieces were added, and the mixture was stirred for 30 minutes. Then, 265 L of ethanol was added, and the solution was heated to 85° C. and refluxed by heating for 60 minutes. The solution was centrifuged, and a liquid burdock fruit extract was obtained. This operation was repeated twice, and the obtained liquid extracts were combined and concentrated under reduced pressure. Dextrin was added at 20% to the solid contents of the extract, and the mixture was spray dried. The arctigenin and arctiin contents were 6.2% and 7.1%, respectively, and burdock fruit extract powder (comprising 20% dextrin) with arctigenin/arctiin (weight ratio)=0.89 was thus obtained.

Example 2 Production of Burdock Fruit Extract 2

As an Example of the composition for inhibiting inflammasome activation of the invention, an extract was extracted from burdock fruit. After cutting burdock fruit (enzymatic activity of 8.23 U/g), the pieces which completely passed through a sieve of 9.5 mm were further passed through a sieve of 0.85 mm, and it was confirmed that 75% thereof remained. To 560 L of water which was kept at 30 to 33° C., 80 kg of the cut burdock fruit pieces were added, and the mixture was stirred for 30 minutes. Then, 265 L of ethanol was added, and the solution was heated to 85° C. and refluxed by heating for 30 minutes. The solution was centrifuged, and a liquid burdock fruit extract was obtained. This operation was repeated twice, and the obtained liquid extracts were combined and concentrated under reduced pressure. Dextrin was added at 20% to the solid contents of the extract, and the mixture was spray dried. The arctigenin and arctiin contents were 6.0% and 6.8%, respectively, and burdock fruit extract powder (comprising 20% dextrin) with arctigenin/arctiin (weight ratio)=0.87 was thus obtained.

Example 3 Production of Burdock Fruit Extract 3

As an Example of the composition for inhibiting inflammasome activation of the invention, an extract was extracted from burdock fruit. After cutting burdock fruit (enzymatic activity of 7.82 U/g), the pieces which completely passed through a sieve of 9.5 mm were further passed through a sieve of 0.85 mm, and it was confirmed that 75% thereof remained. To 560 L of water which was kept at 30 to 32° C., 80 kg of the cut burdock fruit pieces were added, and the mixture was stirred for 40 minutes. Then, 258 L of ethanol was added after 60 minutes, and the solution was heated to 85° C. and refluxed by heating for 30 minutes. The liquid was centrifuged, and a liquid burdock fruit extract was obtained. This operation was repeated twice, and the obtained liquid extracts were combined and concentrated under reduced pressure. Dextrin was added at 20% to the solid contents of the extract, and the mixture was spray dried. The arctigenin and arctiin contents were 6.2% and 6.7%, respectively, and burdock fruit extract powder (comprising 20% dextrin) with arctigenin/arctiin (weight ratio)= 0.93 was thus obtained.

Example 4 Production of Burdock Fruit Extract 4

As an Example of the composition for inhibiting inflammasome activation of the invention, an extract was extracted from burdock fruit. After cutting burdock fruit (enzymatic activity of 7.82 U/g), the pieces which completely passed through a sieve of 9.5 mm were further passed through a sieve of 0.85 mm, and it was confirmed that 75% thereof remained. To 560 L of water which was kept at 30 to 32° C., 80 kg of the cut burdock fruit pieces were added, and the mixture was stirred for 30 minutes. Then, 253 L of ethanol was added, and the solution was heated to 85° C. and refluxed by heating for 40 minutes. The liquid was centrifuged, and the obtained liquid extract was obtained. This operation was repeated twice, and the obtained liquid extracts were combined and concentrated under reduced pressure. Dextrin was added at 25% to the solid contents of the extract, and the mixture was spray dried. The arctigenin and arctiin contents were 6.4% and 7.2%, respectively, and burdock fruit extract powder (comprising 25% dextrin) with arctigenin/arctiin (weight ratio)=0.89 was thus obtained.

Example 5 Production of *Forsythia viridissima* Leaf Extract 1

As an Example of the composition for inhibiting inflammasome activation of the invention, an extract was extracted from leaves of *Forsythia viridissima*. To 50 g of finely cut *forsythia* leaves comprising 2.53% arctiin and 0.76% arctigenin, 350 mL of water was added, and the mixture was kept at 37° C. for 30 minutes. Then, 150 mL of ethanol was added, and extraction with heating was conducted for 30 minutes. The solution was subjected to solid-liquid separation using a 100-mesh sieve and then to freeze drying, and 18.62 g of a *Forsythia viridissima* leaf extract having an arctigenin content of 5.62% was thus obtained.

Example 6 Production of *Forsythia viridissima* Leaf Extract 2

As an Example of the composition for inhibiting inflammasome activation of the invention, an extract was extracted from leaves of *Forsythia viridissima*. To 720 g of finely cut *forsythia* leaves comprising 7.38% arctiin and 0.78% arctigenin, 5 L of water was added, and the mixture was kept at 37° C. for 30 minutes. Then, 2.16 L of ethanol was added, and extraction with heating was conducted for 30 minutes. The solution was subjected to solid-liquid separation using a 100-mesh sieve and then to freeze drying, and 343.07 g of a *Forsythia viridissima* leaf extract having an arctigenin content of 9.55% was thus obtained.

Example 7 Granules Containing Burdock Fruit Extract Powder

As an Example of the composition for inhibiting inflammasome activation of the invention, granules were produced using a burdock fruit extract. The granules were produced according to the "Japanese Pharmacopoeia", General Rules for Preparations, section Granules. That is, the following components (1) to (3) were prepared and processed into granules. The granules were divided into 1.5 g portions and packed in an aluminum laminated film, and granules comprising 0.5 g of burdock fruit extract powder per one pack were obtained.

| | |
|---|---|
| (1) Burdock fruit extract powder of Example 2 | 33.3% |
| (2) Lactose | 65.2% |
| (3) Hydroxypropylcellulose | 1.5% |
| Total | 100% |

Example 8 Granules Containing Burdock Fruit Extract Powder

As an Example of the composition for inhibiting inflammasome activation of the invention, granules were produced using a burdock fruit extract. The granules were produced according to the "Japanese Pharmacopoeia", General Rules for Preparations, section Granules. That is, the following components (1) to (3) were prepared and processed into granules. The granules were divided into 3.0 g portions and packed in an aluminum laminated film, and granules comprising 2 g of burdock fruit extract powder per one pack were obtained.

| | |
|---|---|
| (1) Burdock fruit extract powder of Example 2 | 66.7% |
| (2) Lactose | 30.3% |
| (3) Hydroxypropylcellulose | 3.0% |
| Total | 100% |

Example 9 Tablets Containing Burdock Fruit Extract Powder

As an Example of the composition for inhibiting inflammasome activation of the invention, tablets were produced using a burdock fruit extract. The tablets were produced according to the "Japanese Pharmacopoeia", General Rules for Preparations, section Tablets. That is, the following components (1) to (6) were prepared, and the tablets were obtained.

| | |
|---|---|
| (1) Burdock fruit extract powder of Example 2 | 37.0% |
| (2) Crystalline cellulose | 45.1% |
| (3) Carmellose calcium | 10.0% |
| (4) Crospovidone | 3.5% |
| (5) Hydrated silicon dioxide | 3.4% |
| (6) Magnesium stearate | 1.0% |
| Total | 100% |

[Inhibitory Effect of Arctigenin on Inflammasome Activation]

The inhibitory effect of arctigenin on inflammasome activation is shown below.

(Induction of Cell Differentiation)

THP1-Null cells (Invivogen) or THP-1 cells (JCRB Cell Bank), which are NLRP3 inflammasome reporter cell lines derived from human monocytic cells, were cultured in a RPMI medium containing 10% FBS and 4.5% glucose (hereinafter referred to as a THP1 culture medium, SIGMA). The cells were treated with 500 nM PMA (SIGMA) for 3 hours to differentiate the cells into macrophages, and the cells were washed with PBS twice and then used for the following experiment.

(Induction of Inflammasomes)

The THP1-Null cells or the THP-1 cells after the induction of differentiation were suspended in the THP1 culture medium at $1.0 \times 10^6$ cells/mL and seeded in a 96-well microplate at 180 μL per well ($1.8 \times 10^5$ cells/well). The cells were cultured for 72 hours while the medium was changed every 24 hours, and then LPS as a TLR4-stimulating agent was added at 1 μg/mL. After 3 hours of culturing, the supernatants were removed. Arctigenin-containing media (media obtained by adding arctigenin (purified from burdock fruit) to the THP1 culture medium) were added thereto, and the cells were pretreated for an hour. Then, ATP (final concentration of 5 mM, SIGMA), palmitic acid (final concentration of 500 μM, Junsei Chemical Co., Ltd.) or MSU (final concentration of 100 μg/mL, SIGMA) was added as a NLRP3 inflammasome activation agent to the THP1-Null cells. The culture supernatants were collected after an hour in the case of the ATP treatment, after 12 hours in the case of the palmitic acid treatment and after 3 hours in the case of MSU. Poly(dA:dT)/LyoVec (trademark) (final concentration of 5 μg/mL, Invivogen) was added as an AIM2 inflammasome activation agent to the THP-1 cells over 8 hours, and the culture supernatants were collected. The IL-1β concentrations of the culture supernatants were measured using IL-1β reporter cell line HEKBlue (trademark) IL-18/IL-1β cells (Invivogen) or the ELISA method. The caspase-1 concentrations of the culture supernatants were also measured by the ELISA method.

(Measurement of IL-1β)

HEK Blue (trademark) IL-18/IL-1β cells were used for measuring the IL-1β concentrations of the medium supernatants collected after the ATP treatment. HEK Blue (trademark) IL-18/IL-1β cells (Invivogen) were cultured in a DMEM medium (SIGMA) containing 10% FBS and 4.5% glucose and suspended at $2.8 \times 10^5$ cells/mL. The culture supernatants collected for the IL-1β measurement and IL-1β standard solutions (0-1000 pg/mL) each in an amount of 20 μL were put in an empty 96-well microplate, and 180 μL of the HEK Blue (trademark) IL-18/IL-1β cells were added thereto and cultured at 37° C. in a 5% $CO_2$ environment for 24 hours. The culture supernatants each in an amount of 40 μL were put in a new 96-well microplate, and 160 μL of a coloring reagent, QUANTI-Blue (trademark) (Invivogen, a solution prepared at 1 pouch/100 mL), was added. The reaction was advanced at 37° C. for 2 hours for coloration. The absorbance of each well at 655 nm was measured using a microplate reader, and the IL-1β concentration was measured. In addition, for measuring the IL-1β concentrations of the medium supernatants collected after the treatment with palmitic acid, MSU and Poly(dA:dT)/LyoVec (trademark), Quantikine (registered trademark) ELISA Human IL-1β/IL-1F2 (R&D systems (trademark)) was used. After adding the media and the IL-1β standard solutions to an ELISA plate and advancing the reaction following the TDS of the ELISA Kit, the absorbances at 450 nm were measured, and the IL-1β concentrations of the media were calculated.

(Measurement of Caspase-1)

Caspase-1 was measured following the TDS of Quantikine (registered trademark) ELISA Human Caspase-1/ICE (R&D systems (trademark)). The media collected for the caspase-1 measurement and the caspase-1 standard solutions were put in an ELISA plate and reacted. Then, the absorbances at 450 nm were measured, and the caspase-1 contents of the media were calculated.

(Test 1: Effect of Arctigenin on ATP Stimulation)

Using the methods described above, the THP1-Null cells which were inducted their differentiation and treated with LPS were pretreated with arctigenin and then treated with ATP to activate inflammasomes. Then, the released IL-1β amount and the activated caspase-1 amount were measured. Untreated samples (Normals) and samples which were not pretreated with arctigenin (Controls) were used as controls.

Figure 1:
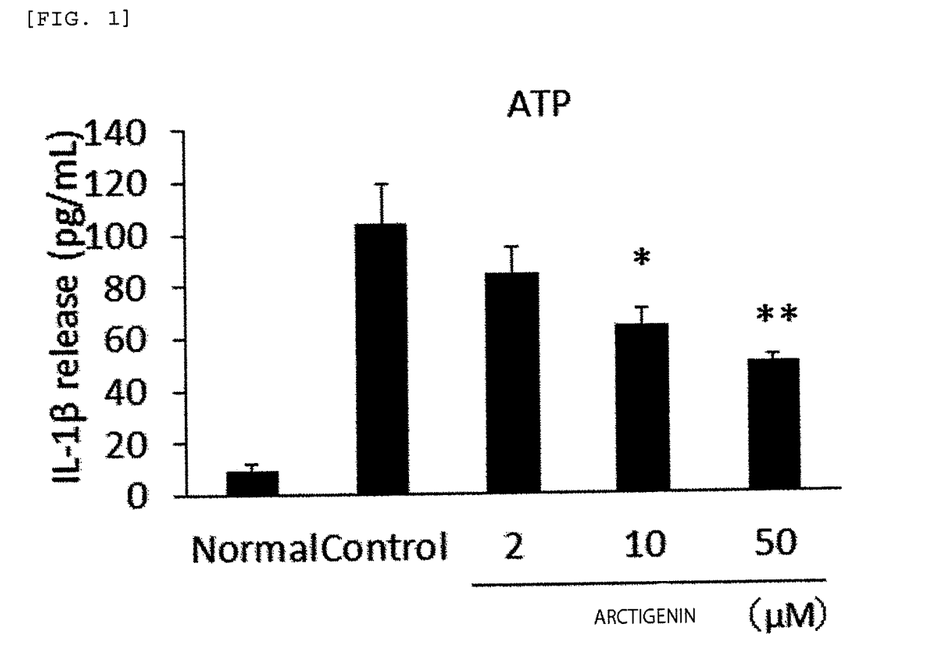
FIG. 1 A graph showing the amount of IL-0 released upon stimulation with ATP when arctigenin treatment was conducted.
Figure 2:
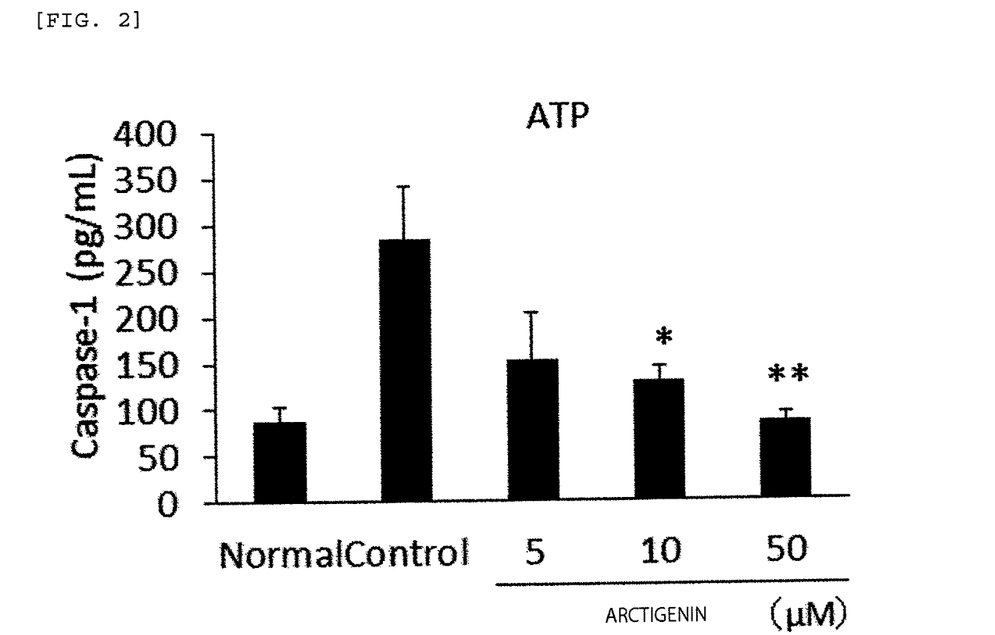
FIG. 2 A graph showing the amount of caspase-1 upon stimulation with ATP when arctigenin treatment was conducted.

FIG. 1 shows the amount of IL-1β released upon the stimulation with ATP when the arctigenin treatment was conducted. FIG. 2 shows the amount of caspase-1 upon the stimulation with ATP when the arctigenin treatment was conducted. In FIG. 1 and FIG. 2, means of three measurements±standard errors (Mean±S.E.M) are shown. As a result of the Dunnett's multiple comparison test (Dunnett's test), "*" is given when the p value was smaller than 0.05 and "**" is given when the p value was smaller than 0.01. As shown in FIG. 1 and FIG. 2, the released IL-1β amount and the caspase-1 amount decreased with significance when the treatment with arctigenin at concentrations of 10 μM and higher was conducted as compared to the values of the samples which were not pretreated with arctigenin (Controls). Thus, it was shown that arctigenin inhibits IL-1β release with significance and inhibits caspase-1 activation with significance, suggesting that arctigenin has the effect of inhibiting inflammasome activation upon stimulation with ATP.

(Test 2: Effect of Arctigenin on Palmitic Acid Stimulation)

Using the methods described above, the THP1-Null cells which were inducted their differentiation and treated with LPS were pretreated with arctigenin and then treated with palmitic acid to activate inflammasomes. Then, the released IL-1β amount and the activated caspase-1 amount were measured. Untreated samples (Normals) and samples which were not pretreated with arctigenin (Controls) were used as controls.

Figure 3:
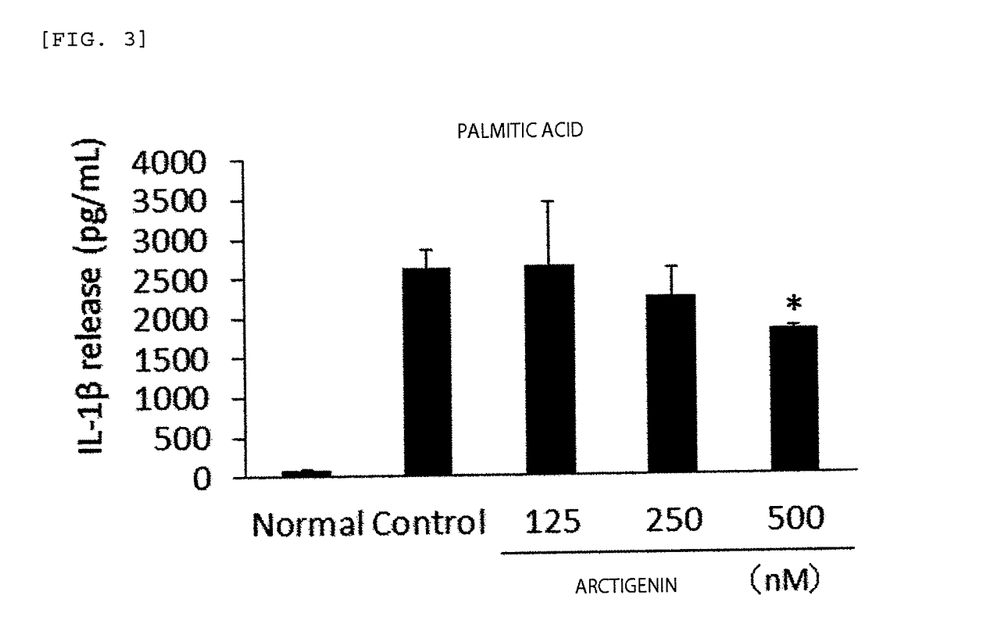
FIG. 3 A graph showing the amount of IL-113 released upon stimulation with palmitic acid when arctigenin treatment was conducted.
Figure 4:
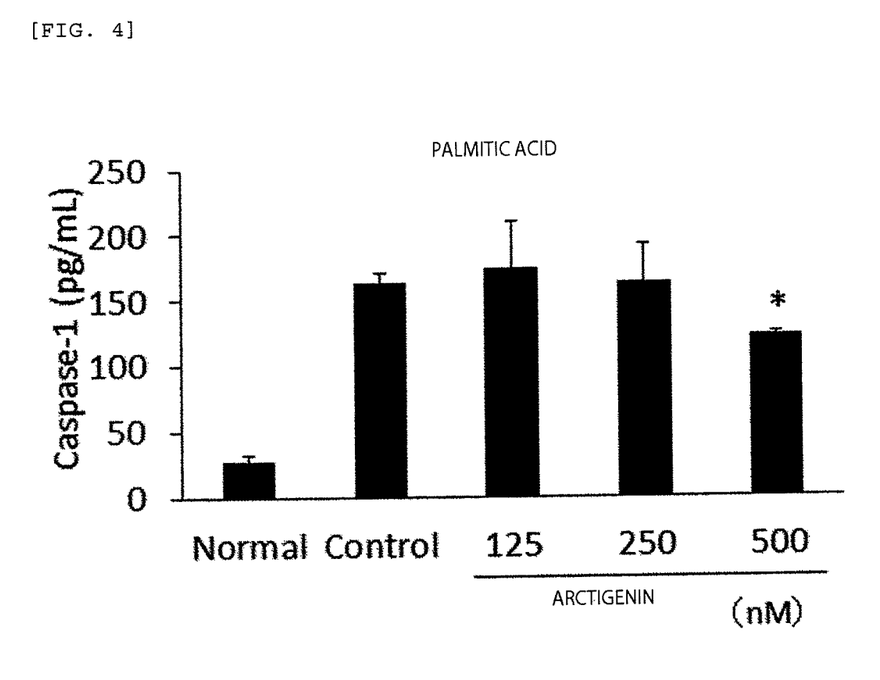
FIG. 4 A graph showing the amount of caspase-1 upon stimulation with palmitic acid when arctigenin treatment was conducted.

FIG. 3 shows the amount of IL-1β released upon the stimulation with palmitin when the arctigenin treatment was conducted. FIG. 4 shows the amount of caspase-1 upon the stimulation with palmitic acid when the arctigenin treatment was conducted. In FIG. 3 and FIG. 4, means of three measurements±standard errors (Mean±S.E.M) are shown, and "*" is given when the p value was smaller than 0.05 as a result of the Student's t-test. As shown in FIG. 3, the released IL-1β amount and the caspase-1 amount decreased with significance when the treatment with arctigenin at the concentration of 500 nM was conducted as compared to the values of the samples which were not pretreated with arctigenin (Controls). Thus, it was shown that arctigenin inhibits IL-1β release upon caused by treatment with a saturated fatty acid with significance and inhibits caspase-1 activation with significance, suggesting that arctigenin has the effect of inhibiting inflammasome activation upon stimulation by a saturated fatty acid.

(Test 3: Effect of Arctigenin on MSU Stimulation)

Using the methods described above, the THP1-Null cells which were inducted their differentiation and treated with LPS were pretreated with arctigenin and then treated with MSU to activate inflammasomes. Then, the released IL-1β amount and the activated caspase-1 amount were measured. Untreated samples (Normals) and samples which were not pretreated with arctigenin (Controls) were used as controls.

Figure 5:
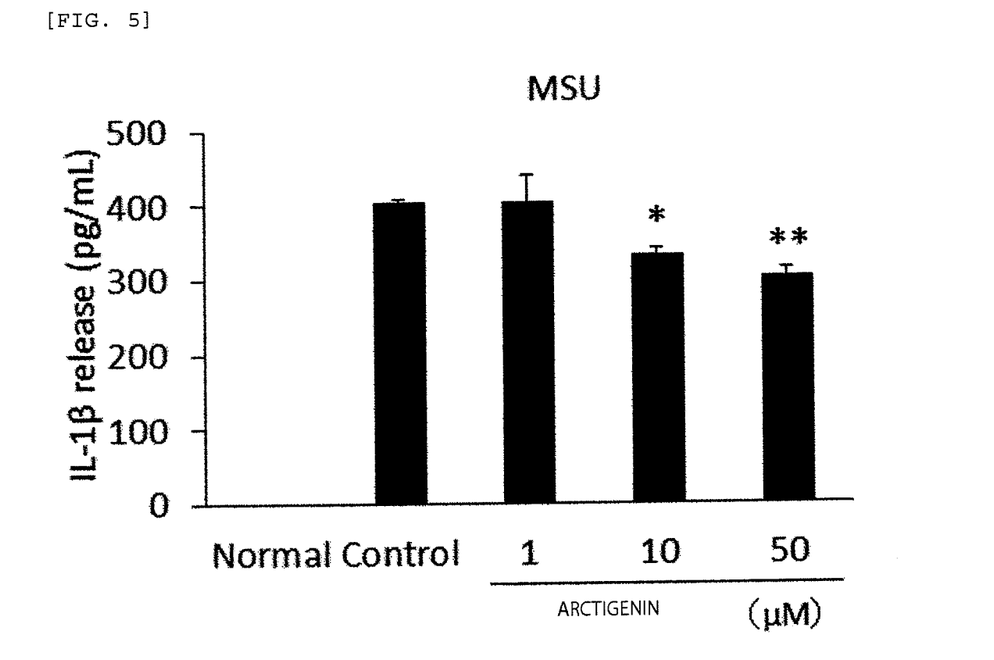
FIG. 5 A graph showing the amount of IL-113 released upon stimulation with MSU when arctigenin treatment was conducted.
Figure 6:
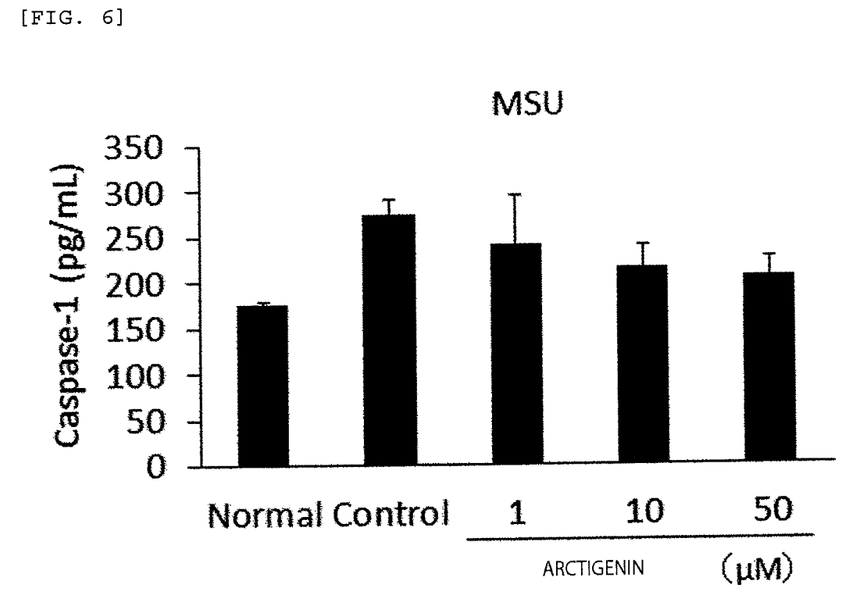
FIG. 6 A graph showing the amount of caspase-1 upon stimulation with MSU when arctigenin treatment was conducted.

FIG. 5 shows the amount of IL-1β released upon the stimulation with MSU when the arctigenin treatment was conducted. FIG. 6 shows the amount of caspase-1 upon the stimulation with MSU when the arctigenin treatment was conducted. In FIG. 5 and FIG. 6, means of three measurements±standard errors (Mean±S.E.M) are shown. As a result of the Dunnett's multiple comparison test (Dunnett's test), "*" is given when the p value was smaller than 0.05 and "**" is given when the p value was smaller than 0.01. As shown in FIG. 5 and FIG. 6, the released IL-1β amount decreased with significance when the treatment with arctigenin at concentrations of 10 μM and higher was conducted as compared to the value of the sample which was not pretreated with arctigenin (Control), and the caspase-1 amount similarly decreased concentration-dependently. Thus, it was shown that arctigenin inhibits IL-1β release upon MSU treatment with significance and inhibits caspase-1 activation, suggesting that arctigenin has the effect of inhibiting inflammasome activation caused by MSU treatment.

The results of Tests 1 to 3 strongly suggest that arctigenin has the effect of inhibiting the activation of inflammasomes including NLRP3.

(Test 4: Effect of Arctigenin on Poly(dA:dT) Stimulation)

Using the methods described above, the THP-1 cells which were inducted their differentiation and treated with LPS were pretreated with arctigenin and then treated with Poly(dA:dT) to activate inflammasomes. Then, the released IL-1β amount and the activated caspase-1 amount were measured. Untreated samples (Normals) and samples which were not pretreated with arctigenin (Controls) were used as controls.

Figure 7:
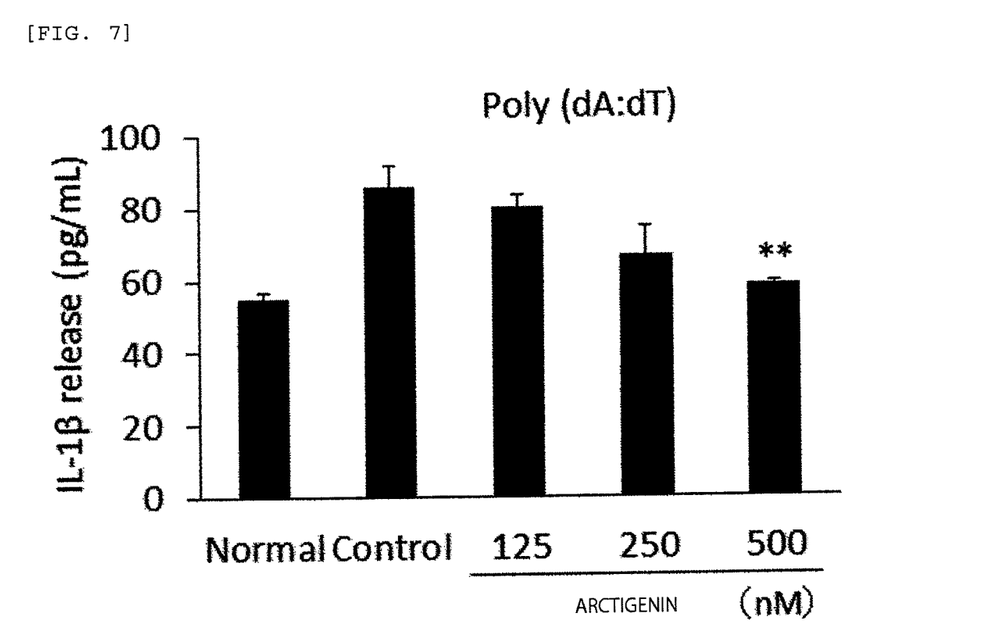
FIG. 7 A graph showing the amount of IL-113 released upon stimulation with Poly(dA:dT) when arctigenin treatment was conducted.
Figure 8:
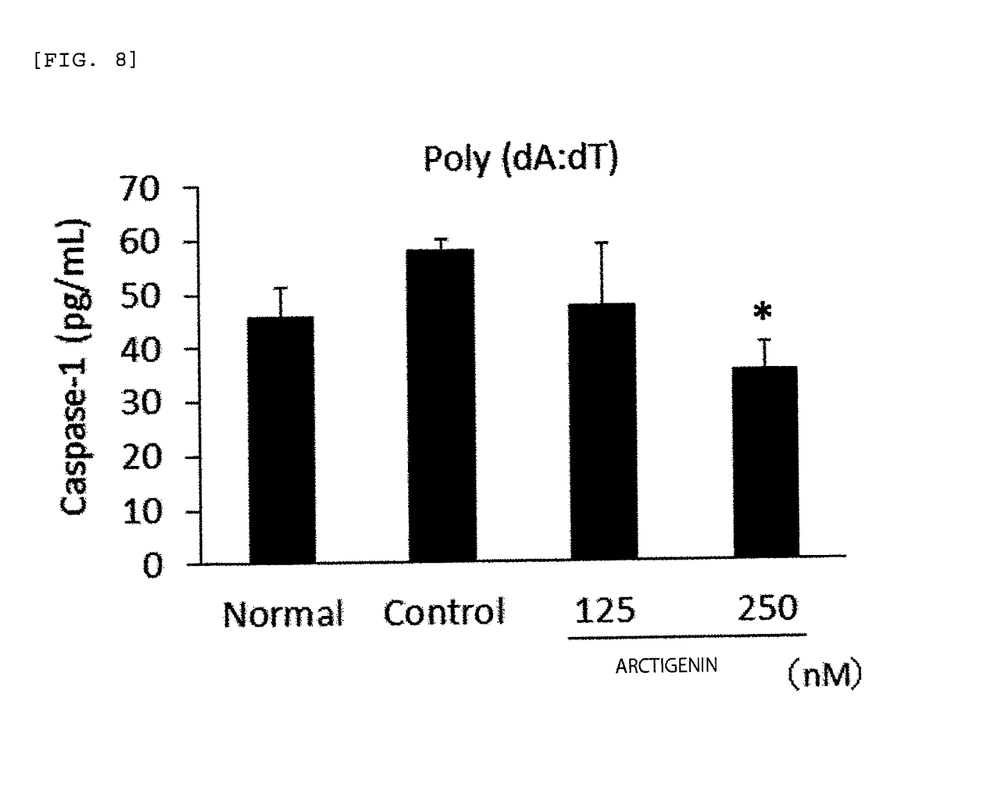
FIG. 8 A graph showing the amount of caspase-1 upon stimulation with Poly(dA:dT) when arctigenin treatment was conducted.

FIG. 7 shows the amount of IL-1β released upon the stimulation with Poly(dA:dT) when the arctigenin treatment was conducted. FIG. 8 shows the amount of caspase-1 upon the stimulation with Poly(dA:dT) when the arctigenin treatment was conducted. In FIG. 7 and FIG. 8, means of three measurements±standard errors (Mean±S.E.M) are shown, and "*" is given when the p value was smaller than 0.05 as a result of the Student's t-test. As shown in FIG. 7, the released IL-1β amount decreased with significance when the treatment with arctigenin at the concentration of 500 nM was conducted as compared to the value of the sample which was not pretreated with arctigenin (Control). Moreover, as shown in FIG. 8, the caspase-1 amount decreased with significance when the treatment with arctigenin at the concentration of 250 nM was conducted. Thus, it was shown that arctigenin inhibits IL-1β release and caspase-1 activation upon Poly(dA:dT) treatment with significance, suggesting that arctigenin has the effect of inhibiting inflammasome activation upon Poly(dA:dT) treatment. That is, it was suggested that arctigenin has the effect of inhibiting the activation of inflammasomes including AIM2.

These results strongly suggest that arctigenin has the effect of inhibiting inflammasome activation independently of the kind of stimulation. That is, it was strongly suggested that arctigenin has the effect of inhibiting inflammasome activation independently of the kind of receptor contained in the inflammasome.

INDUSTRIAL APPLICABILITY

The inhibitor of inflammasome activation and the composition for inhibiting inflammasome activation of the invention can be used for a pharmaceutical product, a cosmetic product and a food for treating, improving or preventing a disease such as infectious diseases, autoinflammatory diseases, allergic diseases, age-related macular degeneration, cardiovascular diseases, ischemic injury, gout, dementia, diabetes, steatohepatitis, arteriosclerosis, other obesity-related inflammatory diseases and inflammatory skin diseases (psoriasis, alopecia, acne vulgaris, atopic dermatitis and the like) and a condition thereof.

The invention claimed is:

1. A method for treating or improving non-alcoholic steatohepatitis (NASH) through inhibition of inflammasome activation including administering arctigenin and/or arctiin to a subject in need thereof, wherein arctigenin and/or arctiin inhibits release of inflammatory cytokines as IL-1αa, IL-1β, IL-6, IL-18, IL-33, TNF-α, and HMGB1 in the subject after administration.

2. The method for inhibiting inflammasome activation according to claim 1, wherein only arctiin is administered to the subject.

* * * * *

UNITED STATES PATENT AND TRADEMARK OFFICE
CERTIFICATE OF CORRECTION

PATENT NO. : 11,376,235 B2
APPLICATION NO. : 16/076092
DATED : July 5, 2022
INVENTOR(S) : Watanabe et al.

It is certified that error appears in the above-identified patent and that said Letters Patent is hereby corrected as shown below:

In the Claims

Column 16, Line 28 (Claim 1, Line 5) please change "IL-1αa" to -- IL-1α --

Signed and Sealed this
Sixth Day of December, 2022

Katherine Kelly Vidal
*Director of the United States Patent and Trademark Office*